United States Patent [19]

Stiefel

[11] Patent Number: 4,868,327

[45] Date of Patent: Sep. 19, 1989

[54] SYNTHESIS OF 2-PHENYL-1,3-PROPANEDIOL

[75] Inventor: Frank J. Stiefel, Princeton Junction, N.J.

[73] Assignee: Carter-Wallace, Inc., New York, N.Y.

[21] Appl. No.: 57,457

[22] Filed: Jun. 3, 1987

[51] Int. Cl.[4] .......... C07C 125/04

[52] U.S. Cl. .......... 560/164; 564/259; 568/705; 568/811; 568/927

[58] Field of Search .......... 564/259; 568/927, 705, 568/811; 560/164

[56] References Cited

U.S. PATENT DOCUMENTS

| | | | |
|---|---|---|---|
| 2,884,444 | 4/1959 | Berger et al. | 560/164 |
| 3,051,744 | 8/1962 | Bowers | 560/164 |
| 3,829,463 | 8/1974 | Kornis et al. | 564/259 |
| 4,143,229 | 3/1979 | Sabbatini | 564/259 |
| 4,272,441 | 6/1981 | Keay et al. | 560/164 |

FOREIGN PATENT DOCUMENTS

| | | | |
|---|---|---|---|
| 630412 | 11/1961 | Canada | 560/164 |
| 691753 | 8/1964 | Canada | 560/164 |
| 800619 | 8/1958 | United Kingdom | 560/164 |

*Primary Examiner*—Bruce Gray

*Attorney, Agent, or Firm*—Kevin B. Clarke

[57] ABSTRACT

A novel method for preparing 2-phenyl-1, 3-propanediol and its dicarbamate is disclosed which readily lends itself to commercial production.

1 Claim, No Drawings

SYNTHESIS OF 2-PHENYL-1,3-PROPANEDIOL

This invention relates to a novel method for the synthesis of 2-phenyl-1, 3-propanediol dicarbamate.

The synthesis of 2-phenyl-1, 3-propanediol dicarbamate has in the past been carried out in accordance with the procedures such as those described in U.S. Pat. No. 2,884,444, namely, by the urethane exchange method as follows:

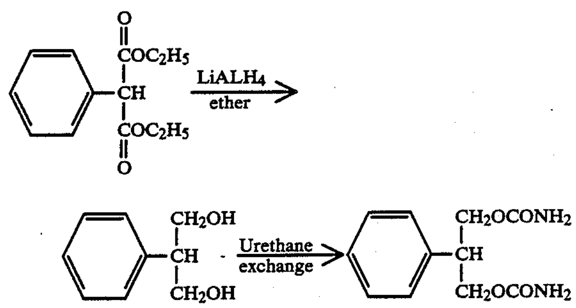

Alternatively, the compound may be prepared by the controlled action of phosgene on 2-phenyl-1, 3-propanediol to form the corresponding dichlorocarbonate derivative with conversion to the dicarbamate by ammoniation. This reaction is advantageously promoted by the addition to the reacting compounds of any suitable acid combining compound such as sodium hydroxide, dialkylaniline, antipyrine and the like. The ammoniation of the dichlorocarbonate derivative to form the dicarbamate is carried out using anhydrous ammonia or aqueous ammonium hydroxide.

The methods described in the patent suffer from several drawbacks on which the inventor as well as chemical manufacturers have expended considerable time and expense in an attempt to improve the synthesis, all of which have been unsuccessful until the present invention.

The principal drawbacks associated with the synthesis disclosed in the prior art are:

The starting material employed in the synthesis is 2-phenyl-1, 3-propanediol obtained by the lithium aluminum hydride reduction of diethyl phenyl malonate. The diethyl phenyl malonate is a relatively expensive material and the lithium aluminum hydride reduction procedure is costly, hazardous and not desirable for tonnage quantities.

It has now been found that the hereinafter disclosed route to 2-phenyl-1, 3-propanediol dicarbamate is an economical and less hazardous procedure than those presently available which readily lends itself to commercial operation.

Example 1 serves to illustrate the preparation of benzaldehyde oxime; wherein the reaction to form benzaldehyde oxime by reacting hydroxylamine sulfate or hydroxylamine hydrochloride with benzaldehyde has been optimized to provide a yield of 95% at 98% purity, which is readily adapted to large scale production, has been realized.

Example 2 describes the preparation of nitromethylbenzene by oxidation of benzaldehyde oxime under controlled conditions to give high yields and a high purity product.

It has been proposed previously to prepare nitromethylbenzene by reacting benzylhalide with silver nitrite or sodium nitrite in dimethyl sulfoxide. Such procedures are expensive, give relatively low yields as well as low purity of product. Moreover, the use of dimethyl sulfoxide presents environmental problems. Further, it has been proposed to prepare nitromethylbenzene by the oxidation of benzaldehyde oxime with trifluroacetic acid and a phosphate buffer. This procedure is also expensive and gives low yields.

In accordance with the present invention, the oxidation of benzaldehyde oxime is accomplished by using either 30% or 50% hydrogen peroxide or preferably commercial 35% peracetic in acetic acid as an oxidizing agent at controlled temperatures of from about 80° C. to about 90° C. to obtain high yields of high purity nitromethylbenzene.

Example 3 describes the further reaction of nitromethylbenzene with formaldehyde to obtain 2-nitro-2-phenyl-1, 3-propanediol.

The literature preparation of the nitrodiol involves the reaction of nitromethylbenzene with formaldehyde, however, in accordance with the present invention, the reaction has been modified whereby a base such as sodium bicarbonate sodium carbonate monohydrate or sodium carbonate is used as the catalyst in lieu of the previously preferred sodium hydroxide. This change in catalyst has been found to allow a more controlled addition of the nitro compound to the formaldehyde with a lessening in the amount of polymeric materials formed in side reactions.

The most critical aspect of the present synthesis is to be found in Example 4, the removal of the aliphatic nitro group from 2-nitro-2-phenyl-1, 3-propanediol.

Prior to the present invention, there was no easy method for the removal of an aliphatic nitro group from a molecule. The prior art methods have included reacting a tertiary nitro compound with tributyltinhydride. The latter reagent is very costly and not conducive to large scale production. Another method proposed is the hydrogenation of a benzylnitro compound with palladium on charcoal at 1200 psi. Debenzylation occurs however, no yield information is available when the reaction was carried out at 1200 psi. When the reaction was carried out at 50 psi, using palladium on charcoal, a mixture containing debenzylated and amino compounds was formed in quantities which preclude the commercial adaptation of the reaction. In accordance with the present invention, it has been discovered that the removal of the aliphatic nitro group may be carried out by the hydrogenation of 2-nitro-2-phenyl-1, 3-propanediol in the presence of palladium on calcium carbonate at 50 psi. The procedure permits the production 2-phenyl-1, 3-propanediol of high purity in yields of about 80%. The method allows for large scale hydrogenation in standard reactors, capable of sustaining 125 psi.

The final reaction of the present synthesis is the conversion of 2-phenyl-1, 3-propanediol to the desired dicarbamate, which is described in Example 5.

The use of phosgene to convert diols to dicarbamates is well known in the prior art. However, such prior art procedures require the presence of an acid acceptor such as sodium hydroxide dimethylaniline or antipyrine. In accordance with the present invention, ethers, e.g., ethyl ether or tetrahydrofuran replace the prior acid acceptors thereby allowing the reaction to be run in benzene, toluene, xylene and the like solutions with no precipitates to be separated and no necessity to recover and purify the acid acceptor.

The method of the present invention is quantitative and precludes contamination of the final product. Moreover, the synthesis is readily adaptable to commercial scale since the chlorocarbonate solution is easily pumped into ammonium hydroxide and removal of the organic solvents easily accomplished by distillation under reduced pressure.

To describe the synthesis of the present invention more particularly, the following non-limiting examples will serve to illustrate the novel synthesis in its preferred embodiments.

EXAMPLE 1

Benzaldehyde Oxime 943 g. (5.75 moles) of hydroxylamine sulfate are placed in a 12 liter flask with 1166 g. (11 moles) of benzaldehyde, 250 ml. of methanol and 5900 ml. of water. The mixture is stirred and chilled to 10° C. in an ice bath. Add 960 g. (12 mole) of 50% sodium hydroxide is added to the mixture gradually over a period of one hour while the temperature of the mixture is maintained below 25° C. with cooling. The mixture is stirred until the reaction is complete (approximately one hour). The mixture is neutralized to pH 7.0 with acetic acid. The lower oxime layer is separated and the aqueous layer is extracted with 2 liters of toluene. The oxime layer and toluene extract are washed twice with 1 liter of water. The toluene is stripped and 1307 g. of the oxime at 98% purity for a 95% yield is obtained.

EXAMPLE 2

Nitromethylbenzene 184.1 g (1.51 mole) of benzaldehyde oxime and 185 ml. of glacial acetic acid are placed in a 3 liter 3 neck flask. The mixture is stirred and heated to 80° C. A solution of 344.1 g. (1.65 mole) of 36.6% peracetic acid and 19 g. of sodium acetate trihydrate is added at a rate such that the temperature is maintained between about 80° and about 90° C. Stirring is continued at about 85° C. for about 3½ hours until there is no oxime. The reaction mixture is chilled to 25° C. and one liter of water is added and the mixture stirred well and the oil which forms, is separated. The aqueous layer is extracted twice with 200 ml. of methylene chloride. The aqueous extract is combined with the oil layer and washed twice with 600 ml. of water and once with 600 ml. of 5% sodium bicarbonate solution, washed again with 400 ml. of water, and dried over sodium sulfate and concentrated to a light orange oil. The yield is 73.5 g. (84%) of 97% pure material by GC.

EXAMPLE 3

2- Nitro-2 Phenyl-1, 3-Propanediol 100 g. (0.73 mole) of nitromethylbenzene, 131.5 g. (1.61 mole) of 37% formaldehyde and 1.8 g. of sodium carbonate monohydrate are placed in a 500 ml. beaker equipped with a mechanical stirrer. The mixture is stirred, the temperature rises to 38° C. and is maintained at 38° C. by using a cold water bath. After 1½ hours, crystals begin to form. The mixture is diluted with 210 ml. of ice water and stirred at 10° C. for about 2 hours. The mixture is filtered and the filtrate washed with water. The damp cake is placed back in the beaker and 280 ml. of ice water is added. The mixture is stirred for 1 hour, filtered and air dried overnight. The solid is stirred with 250 ml. of toluene for about 1 hour at 10° C. and filtered, then washed with cold toluene and dried. The yield is 112.6 g. of nitrophenyldiol (78%), M.P. 96°-97.5° C.

EXAMPLE 4

2-Phenyl-1, 3-Propanediol 12 g. (0.06 mole) of 2-nitro-2-phenyl-1, 3-propanediol, 400 mg. of 5% palladium on calcium carbonate and 150 ml. of methanol are placed in a Parr hydrogenator bottle and reduced with hydrogen overnight. The mixture is filtered through Celite, concentrated to an oil and recrystallized from 30 ml. of toluene. The yield is 7.4 g. (80%) of product, M.P. 52°-4° C.

EXAMPLE 5

2-Phenyl-1-3-Propanediol-Dicarbamate 30.4 g. (0.2 mole) of 2-phenyl-1, 3-propanediol is dissolved in 100 ml. toluene and 35 g. of tetrahydrofuran at room temperature. 30 ml. of phosgene (0.44 moles) is passed into the solution while maintaining the temperature below 25° C. The solution is stirred for about 1 hour at room temperature after the phosgene addition. The tetrahydrofuran solution is dripped into 140 ml. of concentrated $NH_4OH$ held at 0° C. Additional water, i.e., 100 ml may be added to improve the stirring. Stirring is continued for 1½ hours at room temperature and concentrated in vacuo on a steam bath to remove most of the tetrahydrofuran. 150 ml. of water is added and the mixture stirred 1 hour at room temperature. The mixture is filtered, the filtrate washed with water and dried in vacuo at 50° C. Yield 46 g. M.P. 149°-151° C. of crude W-554 (96.6%). Recrystallization from 450 ml. of methanol yields 36 g. of W-554 (75.6%).

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for preparing 2-phenyl-1,3-propanediol comprising forming benzaldehyde oxime by reacting a member selected from the group consisting of hydroxylamine sulfate and hydroxylamine hydrochloride, at reduced temperatures, with benzaldehyde, oxidizing the benzaldehyde oximine thus produced in the presence of an oxidizing agent selected from the group consisting of 30% hydrogen peroxide, 50% hydrogen peroxide and 35% peracetic acid in acetic acid at temperatures ranging from about 80° C. to about 90° C. to produce nitromethylbenzene, reacting said nitromethylbenzene with formaldehyde to form 2-nitro-2-phenyl-1,3-propanediol, removing the aliphatic nitro group from said 2-nitro-2-phenyl-1,3-propanediol by hydrogenation of 2-nitro-2-phenyl-1,3-propanediol in the presence of palladium on calcium carbonate catalyst at elevated pressure to produce 2-phenyl-1,3-propanediol, converting 2-phenyl-1,3-propanediol thus produced to 2-phenyl-1,3-propanediol dicarbamate by treating an ethyl ether or tetrahydrofuran solution of the former with phosgene.

* * * * *